United States Patent [19]

Korpman

[11] 4,394,930

[45] Jul. 26, 1983

[54] ABSORBENT FOAM PRODUCTS

[75] Inventor: Ralf Korpman, Somerset City, N.J.

[73] Assignee: Johnson & Johnson, New Brunswick, N.J.

[21] Appl. No.: 248,387

[22] Filed: Mar. 27, 1981

[51] Int. Cl.$^3$ .................. H05B 3/68; A47J 41/00; B32B 27/00; C08J 9/00

[52] U.S. Cl. .................. 220/444; 220/902; 215/12 A; 215/13 R; 428/35; 428/290; 428/316.6; 428/317.9; 428/319.9; 521/88; 521/149; 604/369

[58] Field of Search ............ 428/35, 290, 316.6, 428/317.9, 319.9; 215/12 A, 13 R; 521/88, 149; 604/369; 220/444, 502

[56] References Cited

U.S. PATENT DOCUMENTS

| | | | |
|---|---|---|---|
| 2,639,239 | 5/1953 | Elliott | 536/87 |
| 2,958,907 | 11/1960 | Mumford et al. | 215/12 A |
| 3,229,769 | 1/1966 | Bashaw et al. | 428/323 |
| 3,247,171 | 4/1966 | Walker et al. | 525/329.4 |
| 3,256,372 | 6/1966 | Adams et al. | 264/28 |
| 3,341,045 | 9/1967 | Sandler | 215/13 R |
| 3,661,815 | 5/1972 | Smith | 525/54.32 |
| 3,681,269 | 8/1972 | Heitz et al. | 210/22 |
| 3,686,024 | 8/1972 | Nankee et al. | 428/286 |
| 3,791,547 | 2/1974 | Branscum | 220/444 |
| 3,878,175 | 8/1975 | Steckler | 128/296 |
| 3,881,489 | 5/1975 | Hartwell | 428/316.6 |
| 3,900,030 | 8/1975 | Bashaw | 604/369 |
| 3,956,224 | 5/1976 | Chu | 525/386 |
| 3,957,362 | 5/1976 | Mancini et al. | 526/230 |
| 4,028,290 | 6/1977 | Reid | 524/845 |
| 4,076,663 | 2/1978 | Masuda et al. | 525/54.31 |
| 4,105,033 | 8/1978 | Chatterjee et al. | 428/317.9 |
| 4,117,184 | 9/1978 | Erickson et al. | 521/149 |
| 4,293,609 | 10/1981 | Erickson et al. | 428/316.6 |
| 4,333,461 | 6/1982 | Muller | 604/369 |

Primary Examiner—William R. Dixon, Jr.
Attorney, Agent, or Firm—Alice O. Robertson; Leonard Kean

[57] ABSTRACT

A foam product having both absorptive and cushioning properties is prepared from a solid, particulate, water-insoluble, water-swellable polymer having a gel capacity of at least 10, a solid, particulate blowing agent, and a liquid polyhydroxy organic compound. Foamable compositions and articles employing the foam are also described.

19 Claims, No Drawings

ABSORBENT FOAM PRODUCTS

The present invention relates to absorbent foam products, compositions and methods of preparation, and articles produced therefrom.

Absorption of mobile aqueous liquids have conventionally been accomplished by the use of sponge or batting. More recently, water-insoluble but water-swellable polymers having high absorptive capacity have been developed. These polymers are granular and have no structural integrity. In U.S. Pat. No. 3,900,030, there is described a catamenial tampon which utilizes an open-celled polymer foam which has the water-swellable polymers imbedded therein. While this provides structural integrity to the absorbent polymer, versatility in application is governed by the foam carrier. Moreover, the method of disposition is dictated by the foam carrier.

DESCRIPTION OF THE INVENTION

In accordance with the present invention it has been discovered that by mixing together a particulate, water-insoluble water-swellable polymer absorbent, a liquid polyhydroxy organic compound and a particulate blowing agent, an absorbent foam product is obtained. In its preparation, from about 25 to 125 parts by weight of the polymer absorbent and from about 2 to 30 parts by weight of the blowing agent are employed for every 100 parts by weight of the liquid polyhydroxy organic compound. The product is superior in absorptive efficiency, is self-supporting, and is degradably disposable as hereinafter described.

The absorbent foam product is a structurally stable solid, resilient and somewhat elastic foam which rapidly swells on absorption of fluid. It differs from conventional sponge or solid foam in having an extremely high capacity for absorbing aqueous fluids, being limited only by the absorptive capability of the polymer absorbent and not by the dimensions of the original foam structure. In addition to the foregoing advantage, the foam has the property of being degradable in large excess of water to water-dispersible particles, providing a convenient means for disposition after the desired function has been accomplished. It is also advantageous in being easily prepared from a non-toxic liquid foam-forming composition which is readily manageable without the necessity of adding water or organic solvent.

In view of the resilient and somewhat elastic nature of the foam, it is also useful in applications where both absorption and cushioning is desired such as in packaging, particularly for odd shape structures. Since the foam may be prepared from nontoxic materials, it is readily adaptable to foaming-in-place. However, the foam is stable and may be prepared in any size and shape, and stored with or without supporting structure. If desired it may be cut to the desired form for ultimate use.

One application of the foam product of the present invention is as a protective liner in dual-walled or dual containers for transporting aqueous fluids in which the inner wall or inner container is of breakable material such as glass used in transporting radioactive solutions or biological fluids. The foam product of the present invention is particularly useful in having both absorptive capabilities and cushioning effect. Moreover, in the case of containers requiring special materials such as outer lead containers for radioactive fluids, it is desirable to reuse the container. In such a situation, the foam is adaptable to being readily disposed of such as by flushing the container with excess water.

Another application for the foam is as absorbent panel material in absorbent articles such as bed pads, sanitary products, diapers, incontinence pads and the like. The foam not only has superior absorptive capabilities but has resilience thereby providing comfort without the thickness of conventional batting. However, it may be employed in combination with wood-pulp panels used in batting and with other absorbent materials, still having the effect of reducing size or thickness. When the foam is to be used as an absorbent panel, it may be applied directly to the ultimate substrate to be employed in the absorbent article, e.g., a diaper backing. Substrates suitable for such purposes include, for example, film such as polyethylene film, non-woven cellulosic materials, wood-pulp materials and the like. A related application employing foam on a flexible substrate is in medical or surgical dressings and sponges.

The water-insoluble, water swellable polymers are lightly cross-linked polymers containing a plurality of hydrophilic groups, such as carboxyl, carboxamide, sulfonate salt or hydroxyl groups, along the polymer chain in sufficient proportions so that the polymer would be water-soluble if it were not for the cross-linking thereof. In these polymers, the hydrophilic groups constitute at least twenty-five percent and up to seventy-two percent of their molecular structure. The materials are not limited by molecular weight range but are of sufficient molecular weight or degree of cross-linking to be water-insoluble while being water-swellable. Many of the suitable materials are those which have been reported to have an average molecular weight per cross-linkage in the range of from about 13,000 to about 300,000. The most common and best known of such materials are polyacrylate modified polysaccharides, cross-linked synthetic polyacrylates, cross-linked carboxymethylcelluloses or cross-linked poly(alkylene oxide)s as hereinafter defined. Other graft polymers or polysaccharides and natural gums such as xanthan gum, locust gum, guar gum and the like or blends thereof are also suitable provided they meet the requirements of water insolubility and water swellability. The water-insoluble, water-swellable polymers have a gel capacity of at least about 10. By "gel capacity" is meant the weight of aqueous fluid which can be imbibed and held per unit weight of polymer, i.e., grams of fluid per gram of polymer. Stated another way, the absorbent polymers have an absorbent capacity of at least 10 times the weight of the material in dry form. The capacity may be up to 500 times or more of the weight of the material in dry form; commonly it is about 15 to 70 times the dry weight. The materials are frequently spoken of in the art as "hydrogels", hydrocolloids" or "superabsorbents". Many of the water-swellable polymers are available commercially.

The polymers are used in particulate form. By "particulate" is meant a substance in the form of fine discrete particles. They may be variously shaped such as spherical, rounded, angular, acicular, irregular, or fibrous. The particles generally range in size from about 1 micron to $2 \times 10^4$ microns in diameter or cross-section (largest dimension when not spherical). The particles are preferably of finely divided powder of particles size from about 1 to $10^3$ microns.

The liquid polyhydroxy organic compound employed in the present invention is a high boiling liquid having at least two hydroxy groups, preferably vicinal or adjacent hydroxy groups. Suitable liquids include glycerol, ethylene glycol, propylene glycol, and the like. Glycerol and ethylene glycol are preferred.

The blowing agent may be any agent decomposing to form a gas on heating and includes sodium bicarbonate and azo compounds, such as azodicarbonamide, p-toluenesulfonyl semicarbazide, p,p-oxybisbenzenesulfonyl hydrazide, p-toluenesulfonyl hydrazide.

In addition to the foregoing essential components, the foam composition may have included therein minor amounts of other additives which may impart desirable properties. Thus, a surface active wetting agent, particularly non-ionic surface active agent may be included to enhance liquid uptake. A surface active agent is of particular advantage in assisting vertical transport of liquids. Representative surface active agents are those commonly described such as alkyl aryl polyether alcohols or alkylphenyl ethers of polyethylene glycol, e.g., reaction product of t-octylphenol or nonylphenol with ethylene oxide. Activated charcoal or other absorbent may be included for odor uptake. Fragance, coloring, etc. may be included for a pleasing effect.

The foam product of the present invention may be prepared by mixing the components in any sequence and then subjecting the mixture to foaming conditions to obtain the desired foam product. Thus, it may be prepared by first mixing together an appropriate water-insoluble, water-swellable polymer and blowing agent, thereafter adding a liquid polyhydroxy organic compound to the dry mixture and then stirring until homogeneous to obtain a foamable composition. Alternatively, the polymer and the liquid polyhydroxy organic compound may be mixed together and the blowing agent thereafter added to obtain a foamable composition. The foamable composition is then subjected to the appropriate time or temperature conditions to obtain the foam product. The conversion of the mixture from a liquid-solid mixture to a foam may take place at ambient temperature over a period from about 1 to 24 hours, or at elevated temperatures, 200° F. to 450° F. (93° C. to 232° C.), preferably about 275° F. to 400° F. (135° C. to 204° C.) for a period of from a few seconds to a few minutes. In producing the foam, the foamable composition may be placed in an appropriate vessel or onto a substrate or surface for foaming, and allowed to foam at the appropriate temperature.

The ultimate foam product may be obtained in any desired shape. Thus, foam products in the shape of a free sheet may be prepared by applying the mixed composition or a metal surface or on a release agent coated surface. A foam-coated substrate may be prepared in a similar manner except that the composition is coated onto the ultimate substrate. For making a foam sheet or foam-coated substrate, any method of application conventionally employed for coating or preparing films, e.g., casting, knife-coating, spray-coating and the like, may be employed. Preferred methods are knife-coating and spray-coating. For use a coating on a substrate, the substrate will be of materials generally employed for absorbent articles such as cellulose, vinyl films, polypropylene, polyester, polyethylene, nylon, metal foils, elastomers, cloth, nonwovens of various fibers, and the like. Coating on a substrate may be of the entire surface of the substrates, in strips or in any other pre-determined pattern. When use as a foam sheet is contemplated, the coating may be made on material previously coated with a release agent such as silicone or on a metal surface. For use in an irregularly shaped device, the liquid composition may be poured into the irregularly shaped area. The coated substrate, the coated sheet-forming surface, or the foamable composition contained in an irregularly shaped device is then subjected to time-temperature related conditions to transform the liquid composition into an absorbent foam product of the desired structure.

Where speed is desired, transformation of the liquid composition to a solid foam may be accomplished by exposure to heat in the range of about 200° to 450° C. for about 1 to 60 seconds. Alternatively, the transformation may be allowed to take place at ambient temperature for time previously set forth. A factor affecting rate of solidification in addition to temperature is the amount of polymer absorbent. Compositions with high absorbent content, e.g., greater than about 50 parts per 100 parts of liquid polyhydroxy compound, solidify and foam at ambient temperature in time measured in hours but with lower amounts of absorbent, there is increase in the time necessary for completion of foam formation. Foams are more quickly formed from the more viscous liquid polyhydroxy compounds. However, the ultimate polymer absorbent content of the foam is generally lower with the more viscous polyhydroxy compound. Thus, for example, a foam obtained from glycerol as polyhydroxy compound may have from 70 to 100 parts by weight of absorbent per 100 parts of glycerol while a foam obtained from ethylene glycol as polyhydroxy compound may have from 80 to 110 parts by weight of absorbent per 100 parts of ethylene glycol.

Many water-insoluble, water-swellable polymers suitable as absorbent are available commercially. They also may be prepared by cross-linking a pre-formed water-soluble, straight chain polymer, by polymerizing an appropriate monomer or a monomer with a co-monomer to effect simultaneous polymerization and cross-linking, or by incorporating a hydrophilic group into a completed polymer. An example of a later incorporation of a hydrophilic group to the completed polymer is the incorporation by sulfonation of a sulfonic acid moiety. When it is desired to have the hydrophilic group in the salt form, the polymer may be prepared first as an acid, ester, amide, or nitrile and the product hydrolyzed in whole or in part.

The preferred polymers have an acrylate group in their molecular structure. They may be completely synthetic acrylate polymers or acrylate modified polysaccharides, e.g., acrylate modified starch or acrylate modified cellulose. By "acrylate modified" is meant that an acrylate polymer or polyacrylate as hereinafter described has been grafted onto the polysaccharide. "Acrylate polymer" or "polyacrylate" as herein employed embraces not only polymers which contain acrylate salt groups but those which also may contain an acrylamide, acrylic acid, acrylic ester group or hydrolyzed acrylonitrile group.

The preferred synthetic acrylate polymer absorbents are those which have a salt group, an acid group, or which have both an amide group and a salt or acid group. These have been represented in the literature, e.g., U.S. Pat. No. 3,686,024 by the following formula:

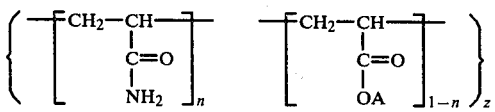

where A is an alkali metal ion such as sodium or potassium, or is hydrogen, n is from about 0.5 to about 0.9, 1-n defines the extent of hydrolysis, and z is the number of mer units between cross-links.

The polyacrylate absorbent containing both amide and carboxylate groups may be prepared either (1) by aqueous polymerization of acrylamide with a difunctional organic cross-linker such as N,N'-methylenebisacrylamide in the presence of a free radical catalyst to obtain a water-swellable, cross-linked polyacrylamide, followed by partial hydrolysis in aqueous alkali to obtain a cross-linked polymer having both an amide and an alkali metal carboxylate groups as more fully described in U.S. Pat. No. 3,247,171, or (2) by cross-linking a previously prepared linear polyacrylamide with a cross-linking compound such as N,N'-methylenebisacrylamide and thereafter hydrolyzing, or (3) by copolymerizing acrylamide and acrylic acid alkali metal salt in the presence of a cross-linking monomer such as N,N'-methylenebisacrylamide and a catalyst system such as 1:1 ammonium persulfate and β-dimethylaminopropionitrile, also described in the aforesaid patent.

Polyacrylate absorbents with carboxylate groups only as functional groups may be prepared by subjecting linear polyacrylate to high energy ionizing radiation cross-linking as described in U.S. Pat. No. 3,229,769, or to chemical cross-linking as described in British Pat. No. 719,330.

Acrylate modified polysaccharides are those which have a polyacrylate chain grafted onto a cellulose or starch molecule. They are preferred graft copolymers of polysaccharides which have hydrophilic chains grafted thereon. By "hydrophilic chain" is meant a polymer chain obtained from monomers which have a group which is water-soluble or becomes water-soluble on hydrolysis, e.g., carboxyl, sulfonic, hydroxyl, amide, amino, quaternary ammonium and hydrolysis products thereof. In the polysaccharides acrylate polymers, a hydrophilic chain of the general formula

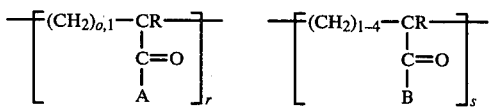

is attached to the backbone of the cellulose or starch molecule through a carbon linkage. In the formula,

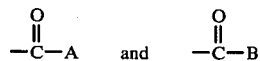

independently represents an acid, ester, alkali metal, ammonium salt or amide group, each R independently is hydrogen or lower alkyl, r is an integer of from 0 to about 5,000 and s is an integer of from 0 to 5,000, and r+s is at least 500. The polysaccharide acrylate polymers may be prepared (a) by polymerizing an appropriate polysaccharide with acrylonitrile or methacrylonitrile, with methyl or ethyl acrylate, with acrylic or methacrylic acid, or with acrylamide or methacrylamide, and thereafter hydrolyzing the resulting polymer in whole or in part with aqueous alkali, or (b) by polymerizing the alkali metal salt of acrylic or methacrylic acid.

The procedures for carrying out graft copolymerization of olefinically unsaturated chains onto cellulose and starch are well known in the art. Grafting of the hydrophilic material onto a starch or cellulose backbone is usually accomplished simultaneously with the formation of the hydrophilic polymeric material and is carried out in the presence of a free radical catalyst system in an aqueous medium, or by irradiation (ultraviolet, gamma-, or X-radiation). Catalyst systems for employment in aqueous media usually comprise an inorganic oxidizing agent as initiator and an inorganic reducing agent as activator.

Representative oxidizing agent initiators are inorganic persulfates, peroxides and alkali metal bromates and chlorates. Representative reducing agent activators are alkali metal bisulfites, sulfites, ferrous ammonium sulfate, and alkali metal thiosulfate.

In one method for carrying out graft polymerization employing a catalyst system, the inorganic oxidizing agent initiator and the inorganic reducing agent activator are alternately added to a reaction medium comprising a water-solution of acrylate monomers and a dispersion of pulverulent or fibrous water-insoluble water-swellable polysaccharide in a mixture of water-immiscible and water-miscible solvents to obtain an acrylate modified polysaccharide product as more fully described in U.S. Pat. No. 4,028,290. Other suitable methods for chemical catalytic graft polymerization may be found in U.S. Pat. Nos. 3,256,372; 3,661,815; 4,076,663; and 4,105,033.

Suitable polysaccharide acrylate polymers are those in which the hydrophilic chain loading on the backbone is in the range of from about 10 percent by weight to about 90 percent by weight, usually from about 40 to 80 percent by weight of the polysaccharide acrylate polymer.

Other suitable water-insoluble, water-swellable polymers include cross-linked carboxymethylcellulose (CMC) obtained as described, for example, in U.S. Pat. No. 2,639,239, cross-linked poly(alkylene oxide) or molecular weight of at least 100,000, obtained as described, for example, in U.S. Pat. No. 3,956,224, and blends of organic substances of polysaccharide character, e.g., natural or synthetic gums. It has been found generally that when gums are employed they must be employed as blends. It appears that the polysaccharide gums which are normally soluble interact when employed as blends to have the desirable swellability without the undesirable solubility. Typical gums which may be employed in blends include locust bean gum, guar gum, xantham gum, tragacanth gum, karaya gum and the like. Gum blends as well as the absorbent polymers above described are available commercially under various trade names.

The water-insoluble, water-swellable polymers prepared by any of the foregoing methods are generally obtained as stiff, brittle solids. These may be comminuted to the appropriate size. Preferably they are employed in the form of powder as previously defined, but may also be employed in other forms.

The following examples illustrate the invention but are not to be construed as limiting.

EXAMPLES I–VIII

Foamable compositions as set forth in Table A are first prepared, by first mixing together at ambient temperature the appropriate absorbent and blowing agent, thereafter adding the appropriate liquid polyhydroxy organic compound, and mixing to a smooth dispersion.

TABLE A

| Component | I | II | III | IV | V | VI | VII | VIII |
|---|---|---|---|---|---|---|---|---|
| Absorbent | | | | | | | | |
| Starch Polyacrylate (SPC 502S, Henkel) | | | | | | | 50 | |
| Starch Polyacrylate (Stasorb ®, A. E. Staley) | | | | | | 50 | | |
| Cross-linked Ionic Polyacrylate (Permasorb ® AG, National Starch) | 50 | 75 | 50 | | | | | |
| Polyacrylate (Sanwet ®, Sanyo) | | | | | 50 | | | |
| Polyacrylate (Aqua-Keep, Mitsubishi) | | | | 50 | | | | |
| Cellulose Polyacrylate* | | | | | | | | 50 |
| Polyhydroxy Compound | | | | | | | | |
| Glycerol | 100 | | 100 | 100 | 100 | | | |
| Ethylene Glycol | | 100 | | | | 100 | 100 | 100 |
| Blowing Agent | | | | | | | | |
| Celogen ® OT | | | 5 | | | | | |
| Celogen ® T Sol | | | | 5 | | | | 5 |
| Celogen ® AZ | | | | | 5 | | 5 | |
| Sodium Bicarbonate | 5 | 10 | | | | 5 | | |

*Prepared according to U.S. Pat. No. 3,889,678

In separate operations, portions of each composition are treated in the following manner: (a) knife-coated onto a release-coated paper, (b) knife-coated onto a polyethylene film, and (c) poured into the space between the inner glass and outer metal walls of a dual-wall container until about one-tenth of the space is filled. The treated compositions are allowed to stand at ambient temperature whereupon foaming occurs in a few hours and there are obtained (a) foam sheets from the compositions which have been knife-coated onto release coated paper; (b) foam-coated film from compositions which have been knife-coated onto polyethylene film; and (c) foam in the space near the bottom portion of the double wall container.

The operation is repeated except that the treated samples are exposed to a temperature of about 275° C. for ten seconds to obtain the corresponding foam products.

When water is applied to the foam in the foregoing examples, the foam swells instantaneously to greater than ten times the original size and completely removes free-standing water.

EXAMPLE IX

A foamable composition is prepared by mixing together at ambient temperature 80 parts of starch polyacrylate (Stasorb ®) and 5 parts of sodium bicarbonate, and then adding and mixing 100 parts of glycerol. In separate operations, the composition is knife-coated onto (a) non-woven cellulosic fabric, (b) polyethylene film, and (c) thin layer of wood pulp materials as substrates. The coated substrates are exposed to a temperature of 300° F. for a few seconds to obtain foam coated substrates. The foam coated substrates are then slit into sizes suitable for absorbent articles.

When water is applied to the articles comprising foam coated substrates, there is instantaneous removal of free-standing water and swelling of the foam.

I claim:

1. An absorbent foam product prepared by mixing together a solid, particulate, water-insoluble, water-swellable polymer having a gel capacity of at least 10, a solid, particulate blowing agent, and a liquid polyhydroxy organic compound and allowing the mixture to foam.

2. A product according to claim 1 wherein the particulate water-insoluble, water-swellable polymer is starch polyacrylate.

3. A product according to claim 1 wherein the solid particulate water-insoluble, water-swellable polymer is cellulose polyacrylate.

4. A product according to claim 1 wherein the solid, particulate water-insoluble, water-swellable polymer is polyacrylate.

5. A product according to claim 1 wherein the liquid polyhydroxy compound is glycerol.

6. A product according to claim 1 wherein the liquid polyhydroxy compound is ethylene glycol.

7. A product according to claim 1 wherein from about 25 to 125 parts by weight the particulate, water-insoluble, water-swellable polymer and from about 2 to 30 parts by weight of the solid, particulate blowing agent are employed for every 100 parts by weight of liquid polyhydroxy organic compound.

8. A product according to claim 1 wherein the water-insoluble water-swellable polymer is starch polyacrylate and the liquid polyhydroxy organic compound is ethylene glycol.

9. A product according to claim 1 wherein the water-insoluble water-swellable polymer is polyacrylate and the liquid polyhydroxy organic compound is glycerol.

10. A product according to claim 1 wherein from about 40 to 80 parts by weight of the particulate, water-insoluble water-swellable polymer and from about 2 to about 30 parts by weight of the solid, particulate blowing agent are employed for every 100 parts by weight of liquid polyhydroxy organic compound.

11. A product according to claim 1 wherein the mixture is allowed to foam by standing at ambient temperature for from about 1 to about 24 hours.

12. A product according to claim 1 wherein the mixture is allowed to foam by subjecting the mixture to a temperature in the range of about 200° F. to 450° F. for from a few seconds to a few minutes.

13. A absorbent foam forming composition comprising relative proportions of
(a) 25 to 125 parts by weight of a solid, particulate, water-insoluble, water-swellable polymer having a gel capacity of at least 10 as absorbent,
(b) 100 parts by weight of a liquid polyhydroxy organic compound, and
(c) 2 to 30 parts by weight of a solid, particulate blowing agent.

14. An absorbent article comprising a foam coated substrate, said foam coated substrate obtained by (a) mixing together a solid, particulate, water-insoluble, water-swellable polymer having a gel capacity of at least 10, a solid, particulate blowing agent, and a liquid polyhydroxy organic compound to obtain a foamable composition, (b) coating said composition onto a substrate, and (c) allowing the mixture to foam.

15. An article according to claim 14 in which the foaming is carried out by subjecting the mixture to a temperature in the range of about 200° F. to 450° F. for from a few seconds to a few minutes.

16. An article according to claim 14 in which the substrate is a polyethylene film.

17. An article according to claim 14 in which the substrate is a non-woven cellulosic fabric.

18. An article according to claim 14 in which the substrate is a layer of wood pulp material.

19. A dual walled container for transporting aqueous fluids having a breakable inner wall and a non-breakable outer wall and having in a portion of the space between the two containers walls, a foam prepared by mixing together solid, particulate, water-insoluble, water-swellable polymer having a gel capacityy of at least 10, a solid, particulate blowing agent, and a liquid polyhydroxy organic compound and allowing the mixture to foam.

* * * * *